(12) United States Patent
Chang et al.

(10) Patent No.: US 12,247,049 B1
(45) Date of Patent: Mar. 11, 2025

(54) APPARATUS AND METHODS FOR SOLID PHASE PEPTIDE SYNTHESIS TO MINIMIZE SOLVENT UTILIZATION

(71) Applicant: CSBio Instrumentation Co., Mountain View, CA (US)

(72) Inventors: Yoheng Hanson Chang, Foster City, CA (US); Dario Slavazza, Fremont, CA (US)

(73) Assignee: CSBIO INSTRUMENTATION CO., Mountain View, CA (US)

( * ) Notice: Subject to any disclaimer, the term of this patent is extended or adjusted under 35 U.S.C. 154(b) by 0 days.

(21) Appl. No.: 18/643,247

(22) Filed: Apr. 23, 2024

(51) Int. Cl.
*C07K 1/04* (2006.01)
*B01J 19/00* (2006.01)
*C07K 1/06* (2006.01)

(52) U.S. Cl.
CPC ........... *C07K 1/045* (2013.01); *B01J 19/0046* (2013.01); *C07K 1/061* (2013.01); *B01J 2219/00495* (2013.01); *B01J 2219/00596* (2013.01); *B01J 2219/00725* (2013.01)

(58) Field of Classification Search
None
See application file for complete search history.

(56) References Cited

U.S. PATENT DOCUMENTS 5,362,447 A * 11/1994 Nokihara ............. B01J 19/0046
422/62
5,395,594 A * 3/1995 Nokihara ............... C07K 1/045
422/231

(Continued)

FOREIGN PATENT DOCUMENTS

CN 109569004 A * 4/2019
EP 1270067 A2 * 1/2003 .......... B01J 19/0046
WO WO-2024058924 A1 * 3/2024

OTHER PUBLICATIONS

Broman, Soren Lindbaek et al., "Green Solid-Phase Peptide Synthesis: Oxyma-Triggered Spectrophotometric Monitoring of Residual Piperidine", Organic Process Research & Development (2024) 28 (3), 35 pp. DOI: 10.1021/acs.oprd.3c00339.

(Continued)

*Primary Examiner* — Jennifer A Leung
(74) *Attorney, Agent, or Firm* — INNOVATION CAPITAL LAW GROUP, LLP; Vic Lin

(57) ABSTRACT

A system and method for solid phase chemical synthesis reduces the overall amount of solvent required for the process. In, for example, solid phase peptide synthesis, during deprotection of the bound peptide, a deprotecting agent, such as piperidine in dimethylformamide (DMF) is introduced to the reaction vessel. After deprotection is complete, pure DMF, or other similar wash solvent, is used to wash away the residual piperidine from the reaction vessel. The used wash solvent can be removed from the reaction vessel, warmed to evaporate off the piperidine, and the purified used wash solvent can be cooled and re-introduced into the reaction vessel for a subsequent washing. Thus, instead of using six volumes of DMF for washing six times, for example, a single volume of DMF can be used, purified and reused, thus substantially reducing the volume of DMF needed for washing the deprotecting agent from the reaction vessel.

13 Claims, 2 Drawing Sheets

(56) References Cited

U.S. PATENT DOCUMENTS

| | | | | |
|---|---|---|---|---|
| 7,628,893 | B1* | 12/2009 | Bonser | B01D 5/006 |
| | | | | 203/25 |
| 11,192,086 | B2* | 12/2021 | Nguyen | B01J 19/2465 |
| 2008/0262172 | A1* | 10/2008 | Zhao | C12Q 1/6874 |
| | | | | 526/67 |

OTHER PUBLICATIONS

Collins, Jonathan M. et a., "Total wash elimination for solid phase peptide synthesis", Nat Commun 14, 8168 (2023). https://doi.org/10.1038/s41467-023-44074-5, 11 pp.

* cited by examiner

APPARATUS AND METHODS FOR SOLID PHASE PEPTIDE SYNTHESIS TO MINIMIZE SOLVENT UTILIZATION

BACKGROUND OF THE INVENTION

1. Field of the Invention

Embodiments of the invention relate generally to apparatus and methods for solid phase peptide synthesis. More particularly, embodiments of the invention relate to systems and methods for reducing solvent use during solid phase chemical synthesis, such as solid phase peptide or oligonucleotide synthesis.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Solid phase peptide synthesis typically involves growing a peptide through the sequential reaction of individual amino acids onto the peptide chain. More specifically, an N-protected amino acid is bound to a solid support, the protecting group is removed, the support is washed, an N-protected amino acid is introduced to react with the bound amino acid/peptide, the N-protection is removed, the support is washed, and additional N-protected amino acids are added as the process repeats to grow the desired peptide.

The deprotection involves the introduction of a deprotection chemical to cleave the N-protection from the bound peptide. It is important that all or substantially all of the deprotection chemical is removed, as residual deprotection chemical, such as piperidine, can lead to double insertion of amino acids during the following coupling due to unintentional protection group-removal of the incoming amino acid derivative, or to deletions due to sequestering of the activated amino acid derivative to form the corresponding piperidide. Large volumes of solvent are required to remove the piperidine from the solid support holding the peptide. Often, six or more rinses are needed to achieve the required levels of residual piperidine to avoid issues therewith.

In view of the foregoing, there is a need for a system and method to recover and/or reuse the chemicals used in washing the residual piperidine from the solid support.

SUMMARY OF THE INVENTION

Embodiments of the present invention aim to solve the aforementioned problems in conventional peptide synthesis by providing an apparatus that can recover and purify wash solvent for reuse over multiple washing steps during solid phase synthesis.

Embodiments of the present invention provide a system for reusing solvent in a chemical synthesis apparatus comprising a first pump operable to remove solvent from a reaction vessel of the chemical synthesis apparatus; an evaporator receiving the solvent moved by the first pump; a heating device warming the solvent that is received into the evaporator to formed purified solvent; and a second pump delivering the purified solvent back into the reaction vessel, wherein the heating device warms the solvent above a first temperature and below a second temperature; the first temperature being a boiling point of an impurity in the solvent; and the second temperature being a boiling point of the solvent.

Embodiments of the present invention provide a method for reusing wash solvent in a chemical synthesis device comprising delivering wash solvent to a reaction vessel to mix with the solid support therein; removing the used wash solvent from the reaction vessel, the used wash solvent including an impurity desired to be removed and the wash solvent; transferring the used wash solvent to an evaporator; evaporating away the impurity desired to be removed, leaving purified wash solvent; transferring the purified wash solvent back to the reaction vessel as the wash solvent for a subsequent mixing with the solid support in the reaction vessel; and repeating the removing, the transferring the used wash solvent, the evaporating and the transferring the purified wash solvent steps until a desired level of removal of the impurity desired to be removed is obtained.

Embodiments of the present invention provide a system for reusing wash solvent in a chemical synthesis apparatus comprising a first pump operable to remove used wash solvent from a reaction vessel of the chemical synthesis apparatus; an evaporator receiving the solvent moved by the first pump; a heating device warming the solvent that is received into the evaporator to formed purified solvent; a vent in the evaporator, the vent permitting the impurity in the vapor phase to exit the evaporator; an inert gas supply line fluidly communicating with the evaporator, the inert gas supply line operable to supply an inert gas into the evaporator; a second pump delivering the purified solvent back into the reaction vessel; and a heat exchanger operable to cool the purified solvent prior to delivery back to the reaction vessel, wherein the heating device warms the solvent above a first temperature and below a second temperature; the first temperature being a boiling point of an impurity in the solvent; and the second temperature being a boiling point of the solvent.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Figure 1:
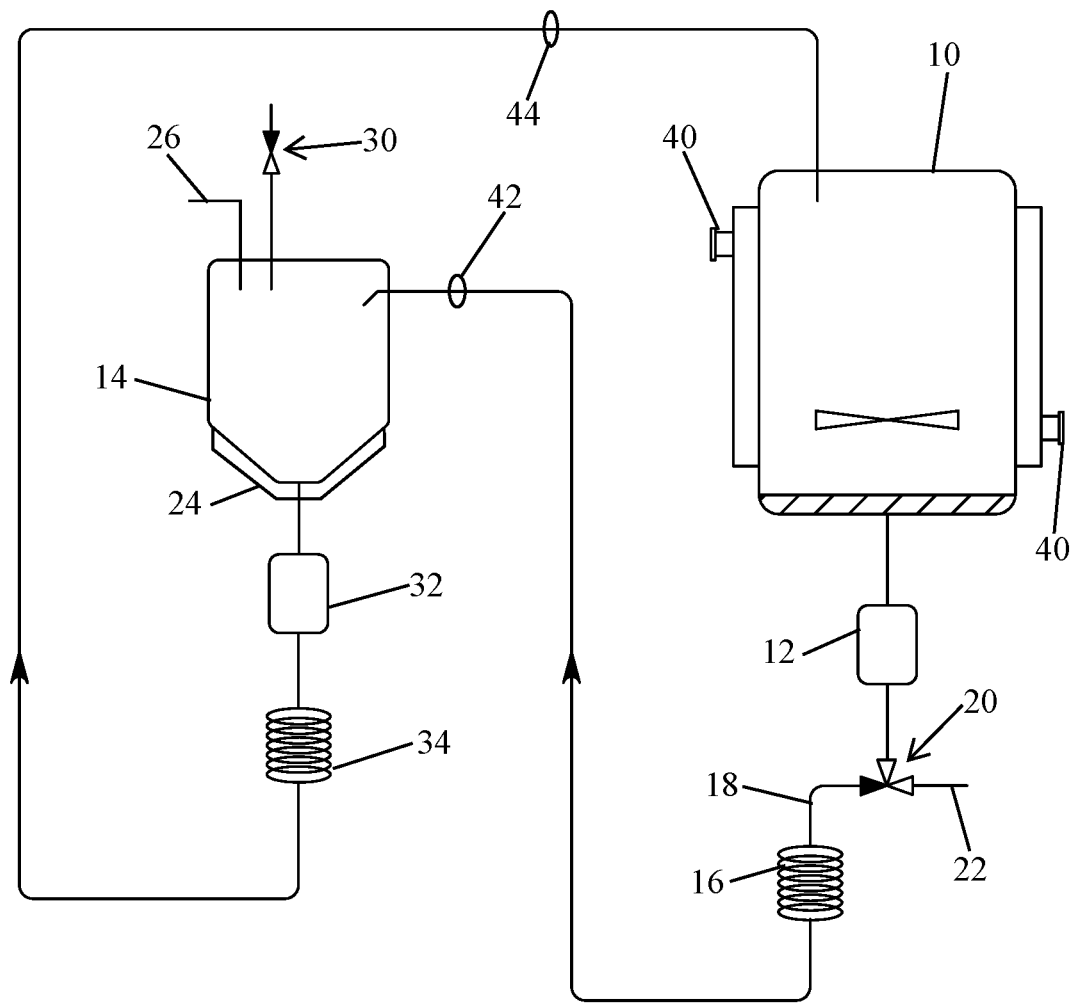
FIG. 1 illustrates a system for reusing and purifying wash fluid in a solid support peptide synthesis system, according to an exemplary embodiment of the present invention.

The illustrations in the figures may not necessarily be drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

As is well known to those skilled in the art, many careful considerations and compromises typically must be made when designing for the optimal configuration of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide a system and method for solid phase chemical synthesis that can reduce the overall amount of solvent required for the process. In solid phase peptide synthesis, for example, during deprotection of the bound peptide, a deprotecting agent, such as piperidine in dimethylformamide (DMF) is introduced to the reaction vessel. After deprotection is complete, pure DMF, or other similar wash solvent, is used to wash away the residual piperidine from the reaction vessel. The used wash solvent can be removed from the reaction vessel, warmed to evaporate off the piperidine, and the purified used wash solvent can be cooled and re-introduced into the reaction vessel for a subsequent washing. Thus, instead of using six volumes of DMF for washing six times, for example, a single volume of DMF can be used, purified and reused, thus substantially reducing the volume of DMF needed for washing the deprotecting agent from the reaction vessel.

The synthesis of peptides or oligonucleotides, for example, can be performed using a solid support, such as a resin, for example, disposed in a reaction vessel. In peptide synthesis, for example, the initial amino acid for the desired peptide may be attached to the solid support at its carboxyl end. The amino end of the amino acid can be protected with a typical protecting group, such as 9-fluorenylmethoxycarbonyl (Fmoc). This protecting group can be cleaved to free the amino end to react with a second N-protected amino acid. This process can be continued to build up the desired peptide.

A deprotecting agent is typically used to remove the protecting group from the amino end of the peptide. The deprotecting agent can be, for example, piperidine in DMF. Typically, about 20% piperidine may be used in DMF (v/v) as the deprotecting agent. The deprotecting agent may be mixed with the solid support holding the N-protected amino acid to remove the protecting group. Once deprotection is complete, it is important to remove the deprotecting agent from the solid support in the reaction vessel. Typically, the solid support, such as a resin, is stirred with pure DMF, which is filtered off. This washing process can be repeated a number of times to ensure removal of all the piperidine. Typically, the piperidine should be removed to less than 1% in the reaction vessel.

In conventional processes, fresh DMF is used for each of the plurality of washes. This can consume significant solvent as the process is repeated.

Figure 2:
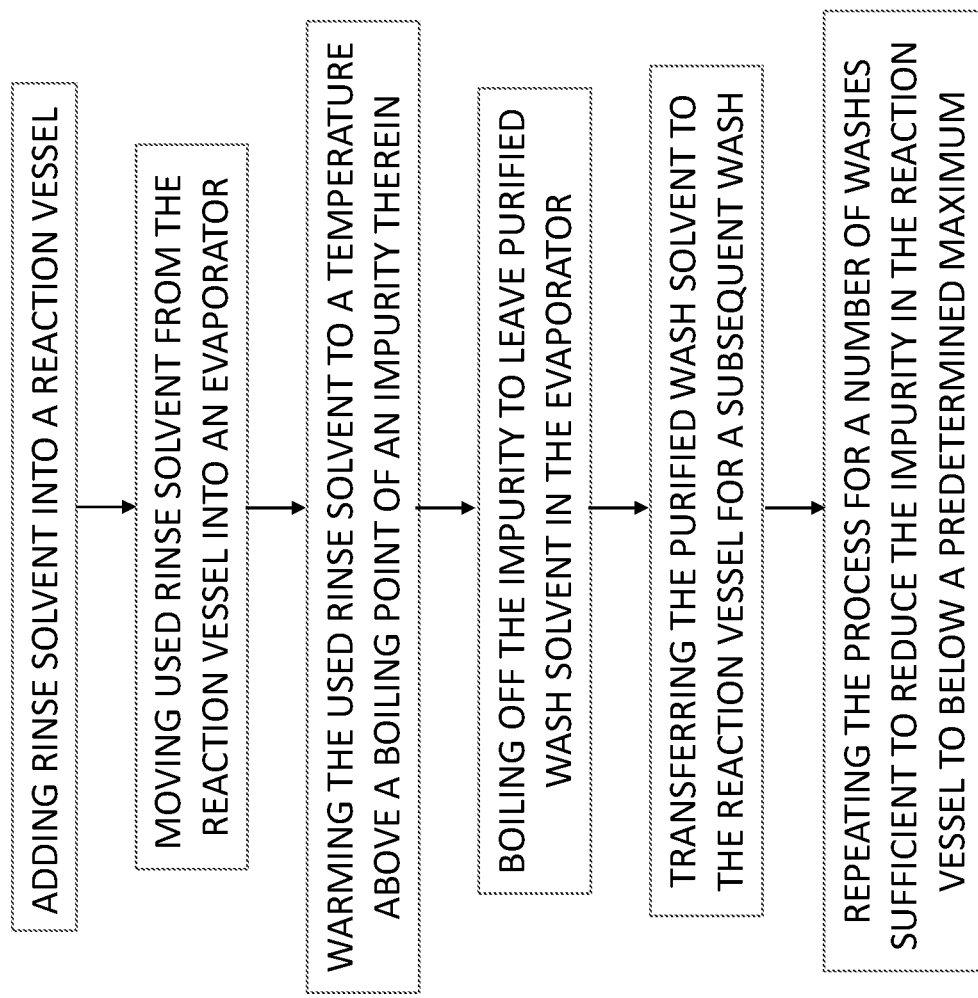
FIG. 2 illustrates a process for synthesizing peptides while reducing solvent consumption, according to an exemplary embodiment of the present invention.

According to aspects of the present invention, and referring to FIGS. 1 and 2, after stirring the resin in DMF in a reaction vessel 10, the DMF is moved, via a pump 12, for example, pumped to an evaporator 14, where the solvent is warmed to at least 106° C., often to at least 110° C., which is greater than the boiling point of the impurity desired to be removed (in this case, piperidine, which boils at 106° C.), and less than the boiling point of the solvent (in this case, DMF, which boils at 153° C.).

In some embodiments, the solvent may be warmed via a heat exchanger 16 formed inline in tubing 18 that fluidly connects the reaction vessel to the evaporator. In some embodiments, the heat exchanger 16 may be used to warm the used wash fluid and the evaporator may include a heating mantle 24, or other similar device, that supplies heat directly to the exterior of the evaporator to further warm or maintain the temperature of the used wash fluid above 106° C., typically at about 110° C. to 120° C., for example.

A release line 26 (also referred to as a vent) may be used to release gaseous piperidine from the evaporator 14. The release line 26 may be used to recover piperidine, via condensation, for reuse as a deprotecting agent. In some embodiments, vacuum may be provided to the evaporator 14, such as through the release line 26. By operating the evaporator 14 under reduced pressure, the removal of the piperidine may be enhanced. In some embodiments, an inert gas, such as nitrogen, may be introduced via valve 30 into the evaporator 14 to help expel the gaseous piperidine out through the release line 26.

After the piperidine is removed from the DMF in the evaporator 14, the fluid can be piped, via pump 32, for example, back to the reaction vessel 10. In some embodiments, a heat exchanger 34 may be used to reduce the temperature of the DMF that is pumped back to the reaction vessel 10 for an additional wash. This temperature reduction may be operable to lower the temperature to about 90° C., often to about 60° C. or possibly even to less than 60° C., for example. The cooling of the solvent prior to reentering the reaction vessel 10 can ensure that the entering solvent is below a temperature that would result in degradation of the synthesis process.

In some embodiments, a temperature sensor 42 may be used to detect a temperature of the solvent after passing through the heat exchanger 16. Further, a second temperature sensor 44 may be used to detect a temperature of the solvent after passing through the heat exchanger 34. These temperature sensors 42, 44 may help automatically regulate the solvent temperature to ensure optimal boil off of the impurity (piperidine) and to ensure proper temperature of the solvent entering the reaction vessel 10.

In some embodiments, this process can be a step-wise process and can be repeated for an appropriate number of rinses, such as from 4 to 10 rinse cycles, for example. In other embodiments, the process is continuous, where solvent is cycled throughout the system, moving between the reaction vessel 10 and the evaporator 14 and releasing the impurity (piperidine) throughout the process.

A valve 20, such as a three way valve, may control the flow of the used wash fluid to the evaporator 14 and can further permit waste to be removed from the closed system via line 22. Accordingly, at the end of the wash cycles, the used DMF wash may be removed as waste or may be further circulated as a wash solvent for the next amino acid addition. A jacket 40 can be provided for maintaining the reaction vessel 10 at an appropriate reaction temperature.

The entire wash system illustrated in the FIG. 1 may be a closed system and can purify the wash solvent by boiling off piperidine outside of the reaction vessel. Such a process can significantly reduce the amount of DMF needed to wash away the deprotecting agent at each step of the building up of the peptide.

As discussed above, the device of the present invention may be used to wash the solid support, such as a resin, after piperidine deprotection. Accordingly, a 20% piperidine in DMF (v/v) may be loaded into the reaction vessel and stirred to deprotect the solid support bound amino acid/peptide. After deprotection, the used wash solution may be pumped out of the reaction vessel and moved to an evaporator. The used wash solution may be heated to 110° C. to remove at least a portion of the piperidine. The reduced piperidine concentration DMF may then be cycled back to the reaction vessel for an additional wash. This cycle can continue until the amount of piperidine present in the reaction vessel is below a desired maximum.

Optionally, the used DMF/piperidine, immediately after deprotection, may be delivered to waste and fresh DMF may be loaded into the reaction vessel and stirred with the solid support to collect piperidine. In this embodiment, the amount of piperidine in the DMF will be below 20%, for example, to begin the evaporation cycle to remove the additional piperidine. In some embodiments, a final wash of the solid support may use fresh DMF to help ensure the piperidine levels in the reaction vessel are below the desired maximum.

Once the piperidine is removed from the DMF to provide purified DMF containing none, or containing less than a predetermined amount of residual piperidine (such as less than 1% piperidine, typically less than 0.5 percent piperidine, often less than 0.01% piperidine), the purified DMF can be stored in the evaporator for use after the next amino acid addition, or, optionally, removed as waste.

In a step-wise fashion, the cycle of washes can be repeated until the piperidine is substantially removed from the reaction vessel. This can take from about 4 to about 10 separate washes of the reaction vessel. As used herein, substantial removal of piperidine from the reaction vessel means less than 2% piperidine, less than 1% piperidine, less than 0.5% piperidine or even less than 0.01% piperidine. In the step-wise embodiment, the used wash solvent can be warmed in the evaporator to drive off a desired amount of piperidine before delivering the purified solvent to the reaction vessel.

In the continuous process, solvent may be cycled through the system shown in FIG. 1, where piperidine is removed from the vent at the evaporator during the cycle, where the concentration of piperidine is continuously lowered as the continuous process is carried out.

Once the piperidine is substantially removed from the reaction vessel, another N-protected amino acid may be charged into the reaction vessel to react with the now deprotected peptide on the solid support.

Once the reaction is complete, piperidine may be added to cleave the N-protecting group, and the reaction vessel may be washed with DMF. This DMF may be either "fresh" (pure) DMF added to the reaction vessel, may be purified DMF from the evaporator, or a combination thereof. The above described process can be repeated for each amino acid addition.

As described above, the DMF may be reused for a predetermined number of reactions (that is, for a predetermined number of amino acid additions) and then removed from the system as waste at the valve 20. This predetermined number of reactions may be a single reaction, a portion of a single reaction (for example, the purified DMF may be used for each wash of the resin, except for the last, where pure DMF is used), or multiple reactions.

The overall result is purification and reuse of DMF for rinsing the resin of residual piperidine after deprotection, requiring substantially less solvent and generating substantially less waste as compared to conventional processes.

EXAMPLE

In a preliminary proof-of-concept study, 200 ml of 80/20 DMF/piperidine mixture was heated to and held at 118° C. for 36 minutes to evaporate out the piperidine. When measuring the solution with 0.01 M Oxyma using an ultraviolet (UV) detector at 498 nm, it was seen that the UV value was 0.117 AU, which is equivalent to 0.01 vol % piperidine.

The correlation between AU absorption and piperidine concentration was determined by linear extrapolation based on multiple known data points. Solutions of piperidine in DMF were made at various concentrations, as shown in the table below, with 0.025M concentration of Oxyma added to each concentration mixture, and AU absorption was determined.

| Piperidine Concentration | UV value (AU) at 495 nm |
|---|---|
| 0.2% | 0.290 AU |
| 0.1% | 0.164 AU |
| 0.05% | 0.068 AU |

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A method for reusing wash solvent used in washing deprotecting agent from a reaction vessel containing a solid support in a chemical synthesis device, the method comprising:
    delivering wash solvent to the reaction vessel to mix with the solid support therein;
    removing the used wash solvent from the reaction vessel, the used wash solvent including deprotecting agent and the wash solvent;
    transferring the used wash solvent to an evaporator;
    evaporating away the deprotecting agent from the evaporator, leaving purified wash solvent;
    transferring the purified wash solvent directly from the evaporator back to the reaction vessel as the wash solvent for a subsequent mixing with the solid support in the reaction vessel; and
    repeating the removing, the transferring the used wash solvent, the evaporating and the transferring the purified wash solvent steps until a desired level of removal of the deprotecting agent in the solid support in the reaction vessel is obtained.

2. The method of claim 1, further comprising permitting the deprotecting agent, in a vapor phase, to exit the evaporator via a vent.

3. The method of claim 2, further comprising condensing and collecting the vapor phase of the deprotecting agent after exiting the vent.

4. The method of claim 2, further comprising introducing an inert gas into the evaporator to drive off the deprotecting agent, in the vapor phase, through the vent.

5. The method of claim 1, further comprising heating the used solvent with at least one of a heat exchanger disposed inline between the reaction vessel and the evaporator, and a direct heating device operable to directly heat an exterior of the evaporator.

6. The method of claim 1, wherein the wash solvent is dimethylformamide and the deprotecting agent is piperidine.

7. A method for synthesizing a polypeptide comprising:
    attaching a first amino acid for the polypeptide to a solid support, at a first carboxyl end, in a reaction vessel;
    adding a deprotecting solution, including a deprotecting agent mixed in a solvent, to the reaction vessel to deprotect an N-protecting group from a first amino end of the first amino acid;
    removing the deprotecting solution from the reaction vessel at the completion of deprotection of the first amino end of the first amino acid;
    transferring the deprotecting solution to an evaporator;
    evaporating away the deprotecting agent in the evaporator, leaving purified wash solvent;
    transferring the purified wash solvent directly from the evaporator back to the reaction vessel as the wash solvent for a subsequent mixing with the solid support in the reaction vessel;
    removing the used wash solvent from the reaction vessel;
    transferring the used wash solvent to the evaporator;
    repeating the evaporating, the transferring the purified wash solvent, the removing the used wash solvent, and the transferring used wash solvent to the evaporator steps until a desired level of removal of the deprotecting agent from the solid support in the reaction vessel is obtained; and
    adding a second N-protected amino acid to react with the deprotected first amino end of the first amino acid.

8. The method of claim 7, further comprising permitting the deprotecting agent, in a vapor phase, to exit the evaporator via a vent.

9. The method of claim 8, further comprising condensing and collecting the vapor phase of the deprotecting agent after exiting the vent.

10. The method of claim 8, further comprising introducing an inert gas into the evaporator to drive off the deprotecting agent, in the vapor phase, through the vent.

11. The method of claim 7, further comprising heating the used solvent with at least one of a heat exchanger disposed inline between the reaction vessel and the evaporator, and a direct heating device operable to directly heat an exterior of the evaporator.

12. The method of claim 7, wherein the wash solvent is dimethylformamide and the deprotecting agent is piperidine.

13. A method for reusing wash solvent used in washing deprotecting agent from a reaction vessel containing a solid support in a chemical synthesis device, the method comprising:
- delivering wash solvent to the reaction vessel to mix with the solid support therein;
- removing the used wash solvent from the reaction vessel, the used wash solvent including deprotecting agent and the wash solvent;
- transferring the used wash solvent to an evaporator;
- evaporating away the deprotecting agent from the evaporator, leaving purified wash solvent;
- transferring the purified wash solvent directly from the evaporator, through a heat exchanger for cooling the purified wash solvent, and directly back to the reaction vessel as the wash solvent for a subsequent mixing with the solid support in the reaction vessel; and
- repeating the removing, the transferring the used wash solvent, the evaporating and the transferring the purified wash solvent steps until a desired level of removal of the deprotecting agent in the solid support in the reaction vessel is obtained.

* * * * *